(12) United States Patent
Månsson et al.

(10) Patent No.: US 7,771,657 B2
(45) Date of Patent: Aug. 10, 2010

(54) SYSTEM, DEVICE AND METHOD FOR DETECTION OF SEVERAL INDIVIDUAL ANALYTES IN A SOLUTION, AND A DISPOSABLE FLOW CELL FOR USE THEREIN

(75) Inventors: Per Månsson, Sollentuna (SE); Henrik Andersson, Sundbyberg (SE); Jan Smith, Stockholm (SE); Kjeld Jensen, Huddinge (SE); Teodor Aastrup, Stockholm (SE)

(73) Assignee: Biosensor Applications Sweden AB, Sundbyberg (SE)

( * ) Notice: Subject to any disclaimer, the term of this patent is extended or adjusted under 35 U.S.C. 154(b) by 0 days.

(21) Appl. No.: 10/517,321

(22) PCT Filed: Jun. 18, 2003

(86) PCT No.: PCT/SE03/01038
§ 371 (c)(1),
(2), (4) Date: Aug. 23, 2005

(87) PCT Pub. No.: WO04/001392

PCT Pub. Date: Dec. 31, 2003

(65) Prior Publication Data

US 2006/0014270 A1    Jan. 19, 2006

Related U.S. Application Data

(60) Provisional application No. 60/389,492, filed on Jun. 19, 2002, provisional application No. 60/389,493, filed on Jun. 19, 2002.

(30) Foreign Application Priority Data

Jun. 19, 2002  (SE)  .................................. 0201876
Jun. 19, 2002  (SE)  .................................. 0201877

(51) Int. Cl.
*G01N 21/00* (2006.01)
*G01N 27/00* (2006.01)
*G01N 31/00* (2006.01)
*G01N 33/22* (2006.01)
*G01N 33/53* (2006.01)
*G01N 33/567* (2006.01)
*C12Q 1/00* (2006.01)
*C12Q 1/68* (2006.01)

(52) U.S. Cl. ........................ 422/82.01; 422/50; 422/57; 422/68.1; 422/81; 422/100; 422/101; 422/102; 422/103; 422/104; 435/4; 435/6; 435/7.1; 435/7.2; 435/287.2; 435/287.3; 435/287.9; 435/288.5; 436/148; 436/149

(58) Field of Classification Search .................. 422/57, 422/81, 82.01, 82.03, 98, 103; 435/288.3–288.5
See application file for complete search history.

(56) References Cited

U.S. PATENT DOCUMENTS 3,585,527 A * 6/1971 Luscher ................ 331/116 FE (Continued)

*Primary Examiner*—Unsu Jung
(74) *Attorney, Agent, or Firm*—Bacon & Thomas, PLLC

(57) ABSTRACT

A system, device and method for detection of several individual analytes in a test solution aliquot (83) with an array of individually operated piezoelectric crystal microbalances are described. The system comprises a connecting station (100) that receives a plurality of individually specific piezoelectric crystal microbalance flow-trough cells (10), each containing a piezoelectric crystal (50) carrying electrodes (56,62) and a coating (66,46) exposing a first member of an interaction pair specific for an individual analyte being a second member of the interaction pair. Flowing means (70) flows a solution (75) and the test solution aliquot (83) to and through a cell compartment of each of the cells (10) via the connecting station (100). Power and measurement means (130) oscillate the piezoelectric crystal(s) (50). A change in oscillating characteristics of the crystal(s) (50), following interaction between the first and second members of the interaction pair, detects presence of the individual analyte(s). Further, disposable flow cells (10) for use in an array of individually operated piezoelectric crystal microbalances (112) is described.

3 Claims, 11 Drawing Sheets

U.S. PATENT DOCUMENTS

| | | | |
|---|---|---|---|
| 4,154,795 A * | 5/1979 | Thorne | 422/99 |
| 4,789,804 A | 12/1988 | Karube et al. | |
| 4,889,611 A * | 12/1989 | Blough, Jr. | 204/411 |
| 5,130,095 A * | 7/1992 | Ricchio et al. | 422/63 |
| 5,494,639 A | 2/1996 | Grzegorzewski | |
| 5,728,583 A * | 3/1998 | Kawakami et al. | 436/69 |
| 5,945,774 A | 8/1999 | Chih et al. | |
| 5,977,687 A | 11/1999 | Tom et al. | |
| 6,078,705 A * | 6/2000 | Neuschafer et al. | 385/12 |
| 6,192,766 B1 * | 2/2001 | Gardhagen et al. | 73/863.12 |
| 6,196,059 B1 | 3/2001 | Kosslinger et al. | |
| 6,287,765 B1 * | 9/2001 | Cubicciotti | 435/6 |
| 6,326,563 B1 * | 12/2001 | Takeuchi et al. | 177/210 FP |
| 2002/0029619 A1 * | 3/2002 | Lee | 73/61.52 |
| 2002/0182631 A1 * | 12/2002 | Schurmann-Mader et al. | 435/6 |
| 2004/0005540 A1 * | 1/2004 | Petrenko et al. | 435/5 |
| 2004/0016297 A1 * | 1/2004 | Paul et al. | 73/580 |
| 2004/0051595 A1 * | 3/2004 | Yoshimine et al. | 331/158 |

* cited by examiner

SYSTEM, DEVICE AND METHOD FOR DETECTION OF SEVERAL INDIVIDUAL ANALYTES IN A SOLUTION, AND A DISPOSABLE FLOW CELL FOR USE THEREIN

The present invention relates to a system, device and method for detection of several individual analytes in a test solution aliquot. The detection is performed with an array of individually operated piezoelectric crystal microbalances with optionally disposable pre-coated flow cells connected to a connecting station.

BACKGROUND

There is a large number of patents directed to the detection of a predetermined chemical or biomolecule in a solution by use of a piezoelectric crystal microbalance, for example, U.S. Pat. Nos. 4,735,906, 4,789,804, and 5,705,399. However, when the presence of several individual chemicals or biomolecules (analytes) are to be determined in the same solution aliquot, then it would be advantageous to have a system, device and method that can simultaneously handle a plurality of microbalances with flow cells which are individually specific for one of the analytes to be detected. Such a system, device and method would be particularly useful for screening of a large number of samples in a short time period, and in cases where the solution aliquot to be tested is small and a number of analytes are to be detected in the same solution aliquot. To avoid time-consuming and less practical regeneration of the cells for multiple use, especially for screening purposes, it would be advantageous to have a disposable pre-coated piezoelectric crystal mounted in a flow cell for screening of a large number of samples. When the sensor surface is inactive after use, the whole flow cell can be replaced.

DESCRIPTION OF THE INVENTION

The invention provides a system, device, and method that enables detection of several individual analytes in a test solution aliquot by use of individually operated piezoelectric crystal microbalances with an interconnected flow path for flowing a solution, and a test solution aliquot, to and through a cell compartment of each microbalance. The system and device comprise a connecting station for receiving and controlling an array of individually specific piezoelectric crystal microbalance flow-through cells. The cells are preferably automatically operatively connected to a flowing unit and a power and measurement unit when they are plugged into the connecting station.

The individually specific piezoelectric microbalance flow-through cells are specific for detection of a predetermined analyte due to at least one activated coating situated within the cell. The piezoelectric crystal carries two electrodes that are used for the oscillation of the crystal. At least one of the electrodes has a coating that exposes a predetermined chemical or biomolecule being the first member of an interaction pair, or the coating will be activated with the first member prior to introduction of the test solution aliquot in case the first member is from start situated at a distance from the electrode, e.g. during transport and storage of a pre-prepared cell. Preferably the pre-prepared cell is a rugged, disposable self-contained flow cell comprising a coated piezoelectric crystal prepared for instant use by plug-in to a connector station capable of providing a flow of fluid in and out of a compartment of the cell as well as oscillation of the crystal by connection to an oscillation unit and signal processing electronics for detection of mass change on the crystal when analyte(s) interacting with the coating is(are) present in the flow.

In case this first member of the interaction pair is covalently or irreversibly immobilized on the electrode coating and the test solution aliquot contains the predetermined analyte and the interaction pair is formed, a change in oscillating characteristics of the crystal is observed and measured due to enhanced mass on the electrode(s). This type of analysis is usually called weight gain assay.

In case this first member of the interaction pair is reversibly bound to the electrode coating and the test solution aliquot contains the predetermined analyte and the interaction pair is formed, a change in oscillating characteristics of the crystal is observed and measured due to loss of mass on the electrode(s). This type of analysis is usually called displacement assay.

A special embodiment of the present invention is when the coating exposing the first member of the interaction pair is situated at a distance from the electrodes and the first member is reversibly bound to the coating. When a second member of an interaction pair is present in the test solution aliquot, the first member is displaced from the coating as it interacts with the second member to form the interaction pair. This interaction pair is displaced from the surface, subsequently attracted and adsorbed by a second coating on the electrode, thus resulting in a measurable mass enhancement on the electrode, measured by a decrease of the frequency and Q-value.

In a presently preferred embodiment of this special embodiment of the invention, the second coating that is situated on one or both of the electrodes is e.g. a protein that attracts and adsorbs an antibody-antigen complex. Examples of such proteins are Protein A and G.

There are several oscillating characteristics that can be measured, e.g. serial capacitance, Q-value and resonance frequencies. Measurements of different oscillating characteristics are previously known in the art of piezoelectric crystal microbalances.

The piezoelectric crystal electrodes comprise a metal surface, which is coated with a coating as described above on one or both electrodes. The metal of the surface is preferably selected from the group consisting of gold, silver, aluminum, nickel, chrome and titan. The crystal of the piezoelectric electrode is e.g. a frequently used quartz crystal, an aluminum nitride (AlN) crystal or a sodium potassium niobiates (NKN) crystal.

Examples of interaction pairs that can be detected in the present invention include anions-cations, antibodies-antigens, receptor-ligand, enzyme-substrate, oligonucleotide-oligonucleotide with complementary sequence, oligonucleotide-protein, oligonucleotide-cell, and peptide nucleic acid (PNA) oligomer—polynucleotide, wherein the polynucleotide may be selected from the group consisting of RNA, DNA and PNA polymers complementary to the PNA oligomer.

The invention further provides a rugged, disposable piezoelectric crystal microbalance self-contained flow cell for use in an array of individually operated piezoelectric crystal microbalances, comprising a coated piezoelectric crystal prepared for instant use by plug-in to a connector station capable of providing a flow of fluid in and out of a compartment of the cell as well as oscillation of the crystal by connection to an oscillation unit and signal processing electronics for detection of mass change on the crystal when analyte(s) interacting with the coating is(are) present in the flow.

Thus, one aspect of the invention is directed to a system for detection of several individual analytes in a test solution aliquot with an array of individually operated piezoelectric crystal microbalances, comprising a connecting station for receiving and controlling an array of individually specific piezoelectric crystal microbalance flow-through cells, wherein each cell comprises a cell compartment containing at least one piezoelectric crystal carrying two electrodes and at least one coating exposing a first member of an interaction pair specific for an individual analyte being a second member of the interaction pair to be detected in the test solution aliquot, the at least one coating being situated on at least one of the electrodes or at a distance from said electrodes in case either or both of the electrodes have a coating other than the coating exposing a first member of an interaction pair, flowing means for uninterrupted flowing of solution and the test solution aliquot to, and through, the cell compartment of each of the individually specific cells via the connecting station; and power and measurement means for individually oscillating the piezoelectric crystal(s) in each of the cell compartments and measuring a change in oscillating characteristics of the crystal(s) following interaction between the first member and the second member of the interaction pair to thereby detect presence of the individual analytes in the test solution aliquot by the individually specific microbalances.

In a presently preferred embodiment of this aspect of the invention the individually operated piezoelectric crystal microbalances are electrostatically and electromagnetically shielded from each other.

In another embodiment the connecting station comprises connection means for serial interconnection of the flowing of the solution and test solution aliquot to and through the cell compartment of the individual cells, and in yet another embodiment the connecting station comprises connection means for parallel connection of the flowing of the solution and test solution aliquot to and through the cell compartment of the individual cells.

Especially when the solution is a salt solution, the system of the invention may further comprise grounding means for electrical grounding of the flow solution and the test solution aliquot to the cell compartment of each of the cells.

In a preferred embodiment of the system of the invention the connecting station comprises a connecting panel having an array of cell connecting receptors, each receptor comprising a receptor connector portion for mating operative engagement with a cell connector portion, each connector portion comprising a pair of electric connecting ports for communication with said power and measurement means and a pair of fluid connecting ports for communication with the flowing means. This is very convenient when the individually specific cells are replaced with new cells, especially when the cells are pre-prepared disposable cells.

In another preferred embodiment of the system of the invention the flowing means comprises a solution feeding and flowing unit having a pump for feeding and flowing the solution from a reservoir via a (first) flow line and a flow valve to a (second) flow line providing a flow of the solution to, and through, each of the cell compartments;

an insertion means for introduction of the test solution aliquot via a (third) flow line, the flow valve and a flow loop to the (second) flow line providing a flow plug of the test solution aliquot to, and through, each of the cell compartments. The insertion means may be any suitable means providing the test solution aliquot to the (second) flow line in a way that does not interrupt the flow to the cell compartments, such as a container containing the test solution and a tube inserted into the solution and via a valve connected to the flow loop or a syringe holding the test solution.

In a preferred embodiment of the system of the invention, the flowing means further comprises a dually functional pulse dampener and degasser downstream of the pump in the (first or second) flow line. Such a dually functional dampener and degasser may be one that has a flow inlet, a flow outlet and an otherwise closed room which has, in addition to the flowing solution, a volume of entrapped gas or air. The volume of entrapped gas or air is e.g. a third to half of the volume of the room.

In a presently preferred embodiment of the invention the first member of the interaction pair is an antibody reversibly bound to the coating and the second member of the interaction pair is an antigen present in the test solution aliquot.

Another aspect of the invention is directed to a multiple piezoelectric crystal microbalance device comprising a connecting station for receiving and individually operating an array of piezoelectric crystal microbalances comprising:

a connecting panel having an array of cell connecting receptors, each receptor comprising a receptor connector portion for mating operative engagement with a cell connector portion of each piezoelectric crystal microbalance flow-through cell, wherein each receptor connector portion comprises a pair of electric connecting ports for communication with a power and measurement means for oscillating a piezoelectric crystal carrying two electrodes in a cell compartment of one operatively engaged flow-through cell and for measuring oscillating characteristics of the piezoelectric crystal; and a pair of fluid connecting ports for communication with flowing means for flowing a solution and a test solution aliquot to, and through, the cell compartment.

In a presently preferred embodiment of the multiple piezoelectric crystal microbalance device according to the invention, the individually operated piezoelectric crystal microbalances are electrostatically and electromagnetically shielded from each other.

In another embodiment of the multiple piezoelectric crystal microbalance device of the invention, the connecting station comprises connection means for serial interconnection of the flowing of the solution and test solution aliquot to and through the cell compartment of the individual cells.

In yet another embodiment of the multiple piezoelectric crystal microbalance device of the invention, the connecting station comprises connection means for parallel connection of the flowing of the solution and test solution aliquot to and through the cell compartment of the individual cells.

In still another embodiment of the multiple piezoelectric crystal microbalance device of the invention, the device further comprises grounding means for electrical grounding of the flow solution and the test solution aliquot to the cell compartment of each of the flow-through cells.

Yet another aspect of the invention is directed to a method of detecting several individual analytes in a test solution aliquot comprising the steps of providing a connecting station with an array of individually operated piezoelectric crystal microbalances having individually specific piezoelectric crystal microbalance flow-through cells, wherein each cell comprises, in a cell compartment containing at least one piezoelectric crystal carrying two electrodes and at least one coating exposing a first member of an interaction pair specific for an individual analyte being a second member of the interaction pair to be detected in the test solution aliquot, the at least one coating being situated on at least one of the electrodes or at a distance from said electrodes in case either or both of the electrodes have a coating other than the coating exposing a first member of an interaction pair, uninterruptedly flowing a solution and the test solution aliquot to, and through, the cell compartment of each of the individually specific cells via the connecting station, individually oscillating the piezoelectric crystal(s) in each of the cell compartments and measuring a change in oscillating characteristics of each crystal, a change in oscillating characteristics of the crystal indicating interaction between the first member and the second member of the interaction pair, thereby detecting the presence of the individual analytes in the test solution aliquot by the individually specific microbalances.

In an embodiment of the method of the invention the flowing of the solution and test solution aliquot to, and through, the cell compartment of each of the individually specific cells, is arranged by serial interconnection of the compartments, and in another embodiment the flowing of the solution and test solution aliquot to, and through, the cell compartment of each of the individually specific cells, is arranged by parallel connection of the compartments.

In a presently preferred embodiment of the invention the first and second members of the interaction pairs are antibodies and antigens. Preferably, the several individual analytes in the test solution aliquot are selected from explosives and narcotics. The explosives may e.g. be selected from the group consisting of trinitrotoluene (TNT), dinitrotoluene (DNT), hexahydro-1,3,5-trinitro-1,3,5-triazine (RDX), octahydro-1,3,5,7-tetranitro-1,3,5,7-tetrazine (HMX), pentaerythritol tetranitrate (PETN), and nitroglycerine (NG), and the narcotics may e.g. be selected from the group consisting of cocaine, heroin, amphetamine, methamphetamine, cannabinols, tetrahydrocannabinols (THC), and methylenedioxy-N-methylamphetamine (Ecstacy).

The invention can also be utilized with cells containing two or more crystals with electrodes or a crystal with two or more electrode pairs thus providing a cell with two or more separate microbalances, which can be used for specific detection of more than two separate analytes.

The invention can also be utilized with cells comprising coatings that have two or more different first members of interaction pairs for detection of at least one of the corresponding second binding partner analytes, e.g. if only detection of any of a number of analytes need to be detected. This is e.g. useful when screening of the occurrence of any of a number of analytes, such as several narcotics or explosives, is made at the same time. This is also the case when the coating is divided into two or more discrete patches, each comprising different exposed first members of interaction pairs.

Still another aspect of the invention is directed to a disposable piezoelectric crystal microbalance flow cell for use in an array of individually operated piezoelectric crystal microbalances comprising:

a sealed cell housing having external fluid and electric connector means for interfacing with external solution flow, electric power and electronic control equipment upon detachably connecting said flow cell to a connecting station of a sensor system, said electronic control equipment being designed for detecting a deviation from oscillating characteristics, such as serial capacitance, Q-value and resonance frequencies, of an oscillating piezoelectric sensor crystal in said housing in response to said crystal changing its mass, said sensor crystal comprising a first face and a second opposite face, each having a respective metal electrode for oscillating said sensor crystal, and having a pair of contact patches for electrically connecting said electrodes to said station via said connector means, the metal surface of the electrode on said first face being the metal surface having a coating; and isolating means for fluidly isolating a compartment comprising the coating in the cell from said contact patches, said fluid compartment being adapted for fluid communication with said station via connector ports of said connector means.

The change in mass on the sensor crystal will normally depend on a change in the composition of the coating on either or both sides of the sensor crystal.

Depending on the desired reaction to occur and to be detected, the coating on the sensor crystal is pre-selected and provided in the flow cell of the invention. In addition to a coating on the sensor crystal, there may be provided additional coatings and/or reaction components and/or stabilizers and/or auxiliary components in the flow cell, selected for each specific need and/or customer desire.

Examples of detectable changing in mass on the sensor crystal is as a result of interaction between a first member of an interaction pair attached to the coating on a metal surface of the sensor crystal and a second member of the interaction pair present in a fluid.

The fluidly isolated compartment may comprise the first member of the interaction pair separated from the coating on the metal surface for activation of the coating with the first-member prior to use. This may improve the shelf life of the flow cell in dry state and the sensitivity in the analysis of analyte. When the flow cell is to be used for analyte detection, a solution is passed through the dry cell thereby releasing the first member of the interaction pair from its position separated from the coating. The first member can be stored in the inlet tube, the walls, the ceiling or a separate compartment in the cell. The first member can be in a dry state or wet state. The free first member is then reversibly activating the coating, which comprises a chemical derivative of the second interaction member with a lower affinity to the first interaction member than the analyte being the second member of the interaction pair, and the flow cell is thereby activated for use in detecting a specific analyte in a fluid.

A special embodiment of this aspect of the present invention is when the coating exposing the first member of the interaction pair is situated at a distance from the electrodes and the first member is reversibly bound to the coating. When a second member of an interaction pair is present in a fluid, the first member is displaced from the coating as it interacts with the second member to form the interaction pair. This interaction pair is displaced from the surface, subsequently attracted and adsorbed by a second coating on the electrode, thus resulting in a measurable mass enhancement on the electrode, measured by a decrease of the frequency and Q-value.

In a presently preferred embodiment of this special embodiment of the invention, the second coating that is situated on one or both of the electrodes is e.g. a protein that attracts and adsorbs an antibody-antigen complex. Examples of such proteins are Protein A and G.

Preferably the first member of the interaction pair is an antibody reversibly bound to the coating, especially an antibody specifically binding to an explosive, such as one selected from the group consisting of trinitrotoluene (TNT), dinitrotoluene (DNT), hexahydro-1,3,5-trinitro-1,3,5-triazine (RDX), octahydro-1,3,5,7-tetranitro-1,3,5,7-tetrazine (HMX), pentaerythritol tetranitrate (PETN), and nitroglycerine (NG), or a narcotic, such as one selected from the group consisting of cocaine, heroin, amphetamine, methamphetamine, cannabinols, tetrahydrocannabinols (THC), and methylenedioxy-N-methylamphetamine (ecstacy).

The coating on the piezoelectric crystal may comprise two or more different attached first members of interaction pairs. With this embodiment of the flow cell screening of the occurrence of any of a number of analytes, such as several narcotics or explosives, can be made at the same time. This is also the case when the coating is divided into two or more discrete patches on the metal electrode each comprising different attached chemically modified derivatives of the first members of interaction pairs.

In a presently preferred embodiment the piezoelectric crystal electrode positioned in the piezoelectric crystal microbalance flow cell of the invention comprises a metal surface, on either or both sides of the crystal, which is coated with a coating comprising one member of an interaction pair. The other member of the interaction pair is an analyte to be detected in an aqueous solution.

The metal of the surface is preferably selected from the group consisting of gold, silver, aluminum, nickel, chrome and titanium. The crystal of the piezoelectric electrode is e.g. a frequently used quartz crystal, an aluminum nitride (AlN) crystal or a sodium potassium niobiates (NKN) crystal.

Examples of interaction pairs that can be detected in the present invention include anions-cations, antibodies-antigens, receptor-ligand, enzyme-substrate, oligonucleotide-oligonucleotide with complementary sequence, oligonucleotide-protein, oligonucleotide-cell, and peptide nucleic acid (PNA) oligomer—polynucleotide, wherein the polynucleotide may be selected from the group consisting of RNA, DNA and PNA polymers complementary to the PNA oligomer.

Upon exposure to the analyte in a fluid, the coating on the metal surface of the piezoelectric crystal will interact with the analyte, either increasing the mass of the coating by attachment of the analyte or the interaction pair, or decreasing the mass of the coating by displacement of the first interaction partner form the coating. This change of mass on the coated metal surface of the electrode is detected by the piezoelectric crystal microbalance sensor and indicates presence of the analyte in the fluid.

The invention can also be utilized with cells comprising electrodes that have two or more different first members of interaction pairs for detection of at least one of the corresponding second member analytes. The electrodes may also comprise only one first interaction member for ensuring detection of just one analyte of interest.

The invention will now be illustrated by some drawings, description or preferred embodiments and examples, but it should be understood that the invention is not intended to be limited to the specifically described details.

DESCRIPTION OF THE PREFERRED EMBODIMENTS

Figure 2:
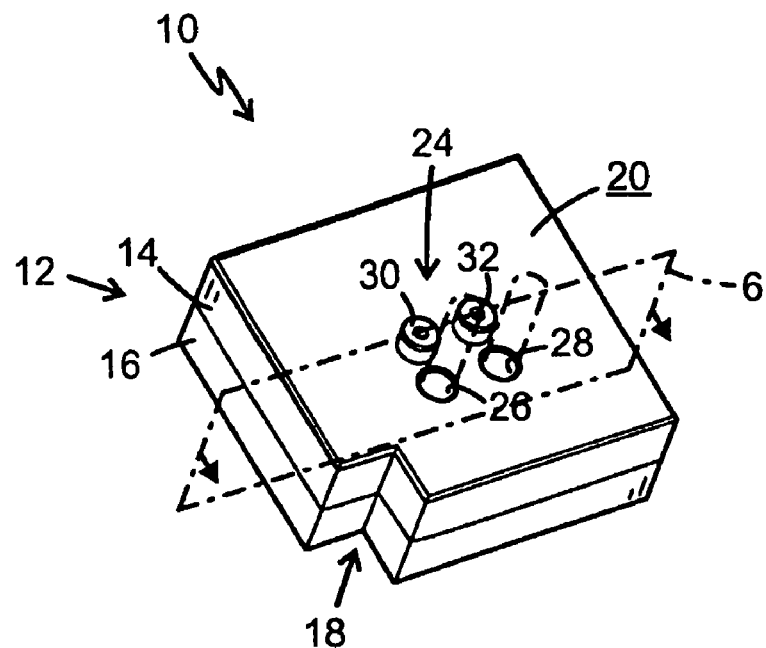
FIG. 2 is a view showing a connecting face of a sensor cell used in the invention.
Figure 3:
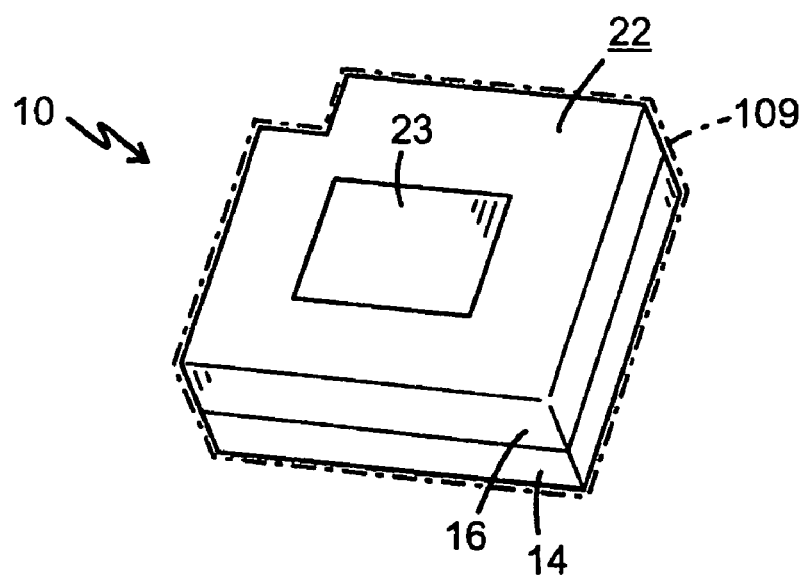
FIG. 3 is a view showing a face of a sensor cell opposite to that of FIG. 2.

A preferred embodiment of a piezoelectric crystal flow cell 10, which is a disposable cell and is suitable for a piezoelectric crystal microbalance used in the invention, is shown in FIGS. 2 and 3. The cell 10 has a housing 12 which may be assembled from a pair of injection-molded halves 14, 16 of plastics material. The halves 14, 16 are permanently sealed.

The cell does not need to have a square or cornered shape as shown but may suitably take other shapes such as circular or oval (not shown). Further, the cell does not need to be disposable nor permanently sealed to function in the present invention.

A rear face 20 of the housing 12 has a central connector portion 24 for connection to a power and measurement means, i.e. power and measurement electronics, 130, and to a solution flowing unit 70 (FIG. 1a) to be later described. The front face 22 of the housing is preferably provided with an identification marking or label 23.

The connector portion 24 has a pair of electric connector ports 26 and 28 flush with the rear face 20 and a pair of fluid connector ports 30 and 32 projecting from the rear face 20. The connector ports 26, 28, 30 and 32 of the cell 10 are adapted for operative engagement with respective complementary shaped connector ports 122, 124, 126, 128 of each of a plurality of cell receptors or connecting sockets 118 (FIG. 8) at a connecting station 100 when the cell 10 is plugged into the socket.

Figure 1A:
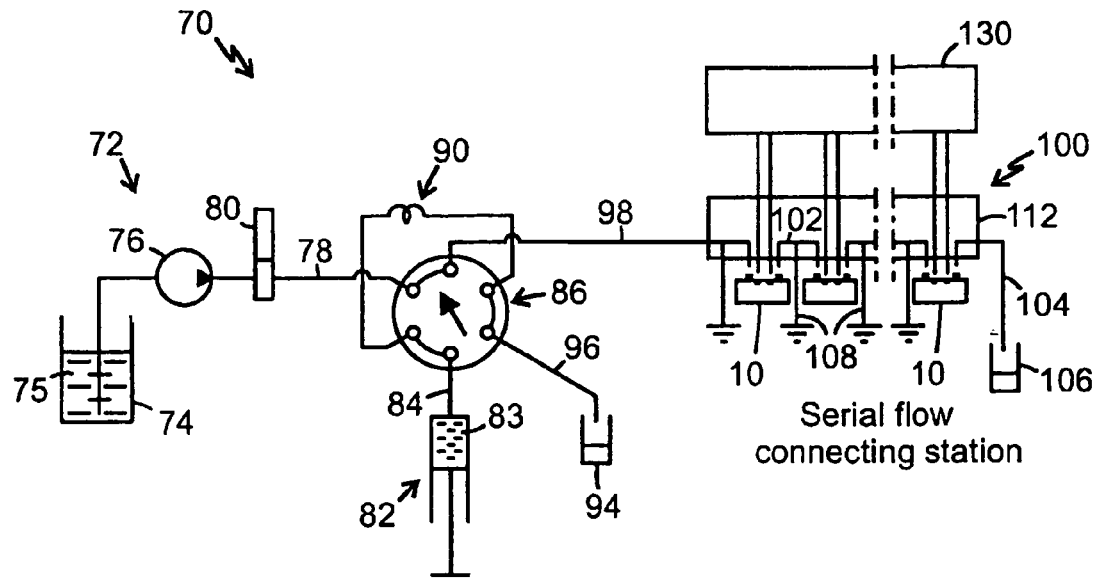
FIG. 1a is a diagrammatic view of a sensor system according to the invention in a test solution insertion state.
Figure 4:
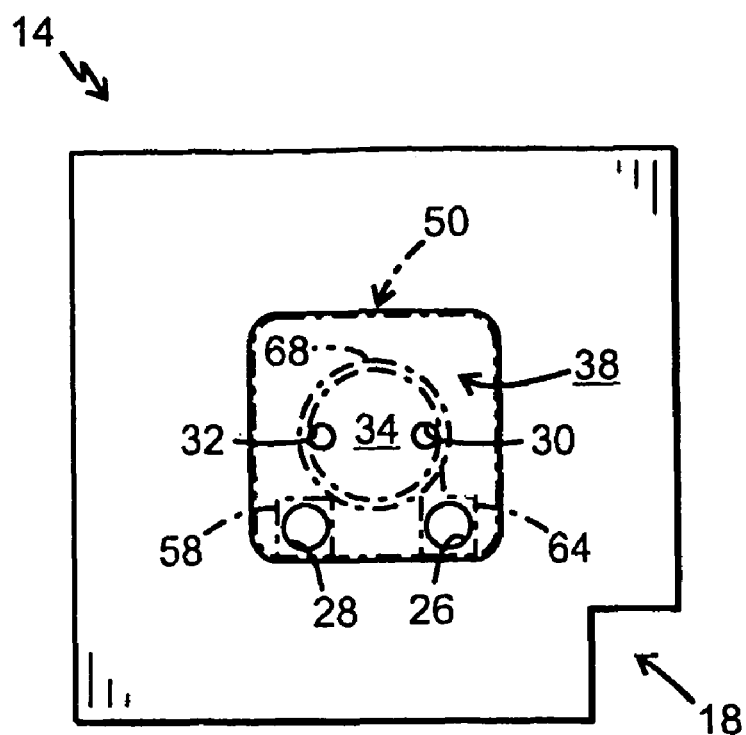
FIG. 4 is an inside plan view of the upper cell half shown in FIG. 2.
Figure 5:
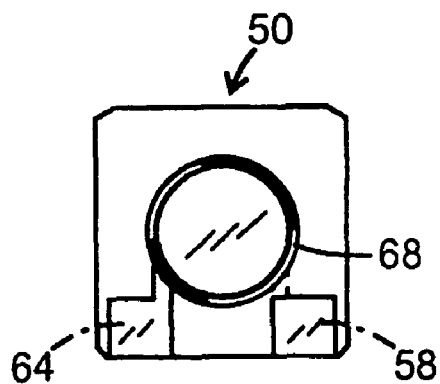
FIG. 5 is a plan view of a sensor crystal used in the invention.

In the embodiment shown in FIGS. 2 and 4, the electric connector ports 26 and 28 comprise through-bores in the cell half 14. The ports 26, 28 enter a closed cavity 38 in the cell half 14 of housing 12 in alignment with respective connector patches 58, 64 of a sensor crystal 50 to be later described, received in cavity 38. When the cell 10 is detachably docked to the station 100 or 101, electric contact pins 114, 116 (FIG. 6) located in the ports 26, 28 contact the respective contact patches 58, 64 and are electrically connected to the power and measurement electronics 130 via the connecting station 100 or 101. The externally projecting pins 114, 116 may be permanently secured, optionally to the connecting station 100 as indicated in FIG. 1a, or to the cell 10 as indicated by phantom lines in FIG. 2. The pins 114, 116 can further be axially spring-loaded in a direction to securely contact the patches 58, 64. Other means of secure electrical contact to patches 58, 64 are possible. For example, the ports 26,28 may be provided with conventional female conducting sockets (not shown)

that are made to contact the patches when the halves 14, 16 are assembled. In the preferred embodiment, however, the contacting pins 114, 116 are made easily interchangeable in order to eliminate decrease in performance due to wearing of the electrical contacting surfaces.

Figure 6:
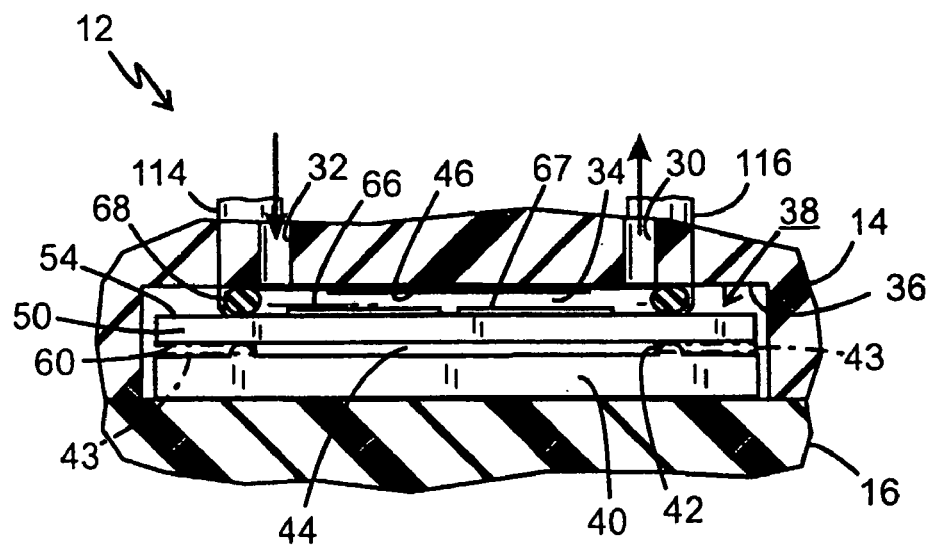
FIG. 6 is a fragmentary view, partly in section along plane 6 of FIG. 2.

In the embodiment shown in FIGS. 2, 4 and 6, the fluid connector ports 30 and 32 also comprise through-bores in the cell half 14. Ports 30, 32 enter a closed, small volume (a few μl) circular compartment 34 in cell half 14 of housing 12. A central portion of sensor crystal 50, an opposite wall 36 of the cavity 38 and an O-ring sealing 68 interposed there between, defines the compartment 34. Compartment 34 is thereby fluidly isolated in the cavity 38 and prevents solution and test solution to reach the contact patches 58, 64. This arrangement allows the solution to be flowed through the compartment 34 via the connector ports 30, 32 in the direction indicated by the arrows in FIG. 6.

Figure 7:
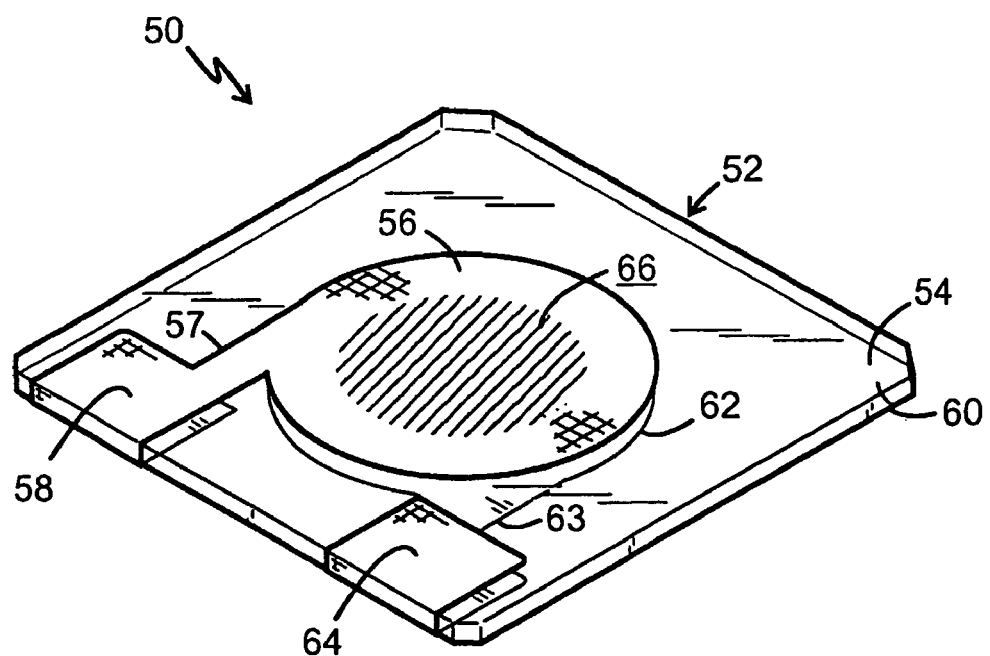
FIG. 7 is another view showing a sensor crystal used in the invention.

The sensor crystal 50 (FIG. 7) is a piezoelectric resonant crystal 52, for example a high Q-value 10 MHz quartz crystal, having deposited on its opposite faces 54 and 60 respective electrodes 56 and 62. By respective conductive paths 57, 63, each electrode 56, 62 is electrically connected to the respective contact patch 58, 64 located on the common face 54 of crystal 52.

By applying AC voltage to the electrodes 56, 62 the crystal 50 will oscillate in a shear mode wave, at a certain resonance frequency. The resonance frequency of the crystal is dependent on the crystal material (for example AT-cut quartz), its thickness, crystal surface coating (electrodes and chemical coating), surrounding medium viscosity, electromagnetic disturbances, electrostatic disturbances as well as temperature and pressure. The principle of detection is to stabilize the crystal oscillation from all the above parameters except for the chemical coating, which can then be monitored in a relative sense by logging of the resonance characteristics in the power and measurement electronics 130.

In the embodiment of FIG. 6, a backing plate 40 supports the opposite face 60 of the crystal 50 mounted in the cavity 38. To allow the crystal 50 to oscillate as freely as possible in compartment 34, backing plate 40 has a peripheral rim or flange 42 defining a hollow space 44 opposite to the compartment 34. In a preferred embodiment, an alternative rim or flange 43 extends radially outwards to the edges of crystal 50 to eliminate mechanical stress from the contact pins 114, 116 by support on the opposite face 60 of crystal. The support may alternatively be restricted to portions opposite the contact pins 114, 116 (not shown). In certain applications, to improve the resonant properties of the crystal, the isolated space 44 may possibly be filled with a viscous fluid. By appropriate dimensioning, this closed design of the cell 10 will mechanically define the applied clamping pressure on the crystal 50, thereby eliminating variation in performance between sensors due to operator dependence.

The electrode 56 facing the compartment 34 is coated with a coating 66. Generally, the coating 66 is adapted to interact, chemically or biochemically, exclusively with a matching particular chemical or analyte possibly present in the test solution 83 resulting in a slight change, increase or decrease, of mass of the crystals. In another embodiment, the opposite wall 36 in the compartment 34 is coated with a complementary or paired coating 46 to supplement the coating 66 as a member of a two-component system in order to activate the cell 10 when exposed to the solution 75. In still another embodiment, the electrode 66 is coated by at least one additional coating 67 (FIG. 6) that, in turn, optionally can also have a complementary separate coating (not shown) in the compartment 34. By such alternative arrangements of multiple or paired coatings, a single cell 10 will be able to detect more than one particular chemical.

The change of mass will slightly alter the oscillating characteristics, e.g. resonance frequency, of the crystal 50, which is detected by a computerized evaluation process in the power and measurement electronics 130.

In operation, when each of one or more cells 10 is plugged into a connecting socket 118 of the connecting station 100 (FIG. 1a and FIG. 8), the crystal 50, electrically connected to the power and measurement electronics 130, is oscillated at its resonant frequency. At the same time, a plug of test solution, i.e. a volume of aqueous test solution trapped between volumes of a solution 75 in fine caliber tubing, flows from the flowing station 70, through the connecting station 100 and enters the compartment 34 in each cell 10. The solution 75, which can be an aqueous solution identical to the test solution 83, has the function of transporting the plug of the test solution aliquot 83 to the cells 10.

Accordingly, if an analyte matching the coating or coatings in the cell compartment 34 is present in the solution 83, the coating(s) will interact with the analyte, and the crystal 50 will change its oscillating characteristics, such as resonant frequency, which is detected and signaled by the power and measurement electronics 130 for further use.

Figure 8:
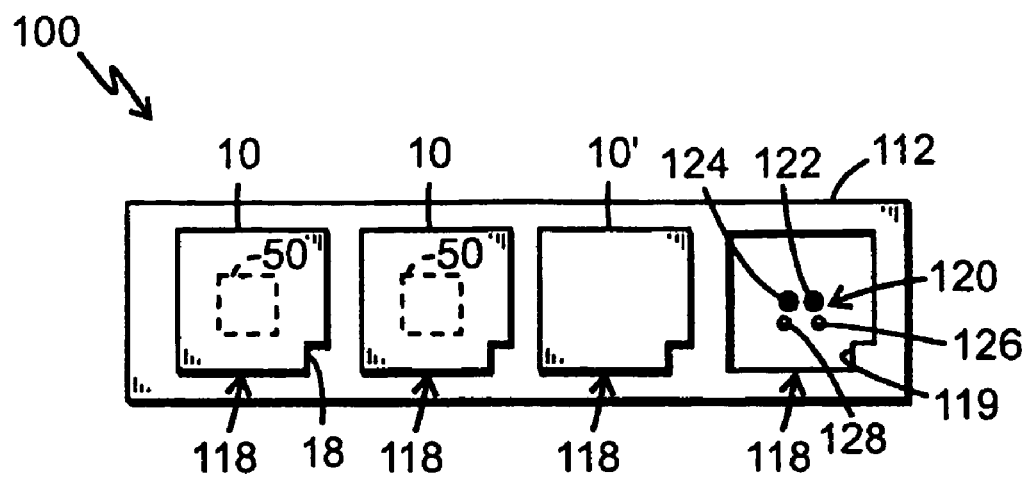
FIG. 8 is a plan view of a connecting station according to the invention.

As shown in FIG. 8, the connecting station 100 is comprised of a connecting rack or panel 112 having a plurality of connecting receptors or sockets 118 for docking a corresponding number of cells 10. Each socket 118 may be shaped as a depression in the panel front and may have a dent 119 to mate with an indent 18 of the cell 10 to prevent improper orientation on insertion of cell 10 in socket 118.

As shown in FIG. 1a, in the preferred embodiment, the sockets 118 of the connecting station 100 are serially connected to the flowing unit 70 in a manifold. More precisely, an inlet flow line 98 to the connecting station 100 will be connected to the inlet port 32 of a cell 10 in the first socket 118, and line segments 102 between each consecutive cell 10 plugged into the station 100 will connect the outlet port 30 of a previous cell 10 with inlet port 32 of the following cell 10. The outlet port of the last cell 10 is connected to a waste reservoir 106 through an outlet line 104. To avoid electric interference between cells 10 caused by electrically conducting solutions 75, 83, the solutions 75, 83 flowing in inlet line 98 and line segments 102 are possibly electrically grounded by grounding conductors 108. To further avoid electric interference including electromagnetic and electrostatic disturbances, the individually operated piezoelectric crystal microbalance cells 10 are totally enclosed by an electric shield 109, for example a metal casing, as schematically shown in phantom in FIG. 3. Preferably, other components of the system are also shielded.

In order to further eliminate cell-to-cell interference, the driving electronics of the power and measurement electronics 130 is tuned such that the liquid or flow side of the crystal 50 is at ground potential.

Figure 1B:
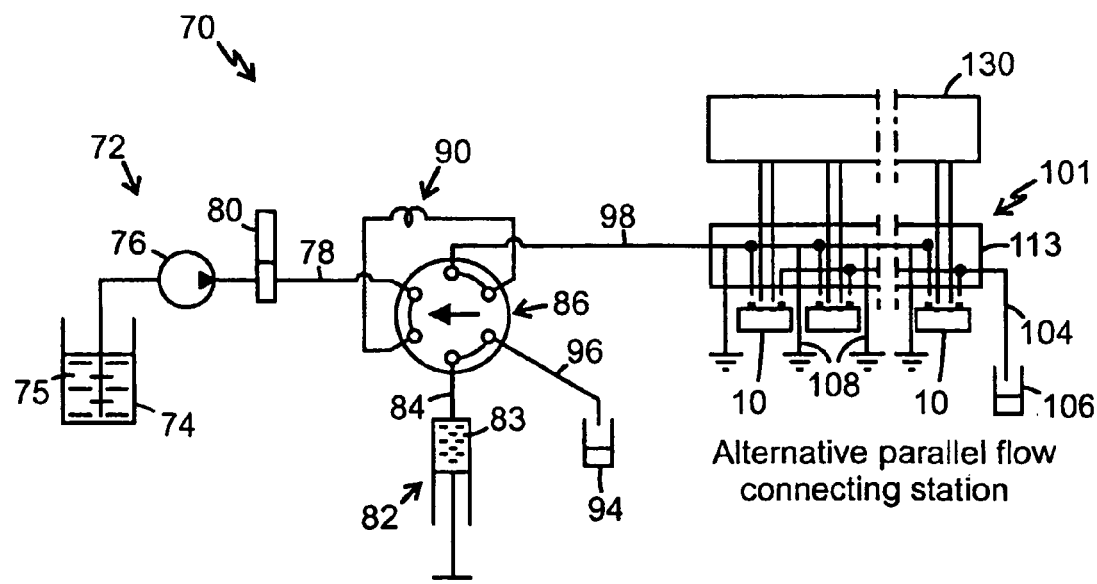
FIG. 1b is a diagrammatic view of a modified sensor system according to the invention in a solution flowing state.

An alternative parallel flow connecting station 101 having a panel 113 for parallel connection of the cells 10 to the flowing unit is diagrammatically shown in FIG. 1b.

While the connecting station 100 may be provided with valve means for automatically shutting off the flow to unused sockets 118 and direct it to the waste reservoir 106, in the preferred embodiment all sockets of the panel 112 should be plugged with cells 10. If by any reason all sockets are not intended to be occupied with functional cells 10 having different coatings for the detection of different chemicals, dummy cells 10' (FIG. 8) having no coatings and crystals but only the compartment and ports (not shown) for passing the flow further, may be used to occupy all unused sockets and direct the flow to the reservoir 106.

Figure 9:
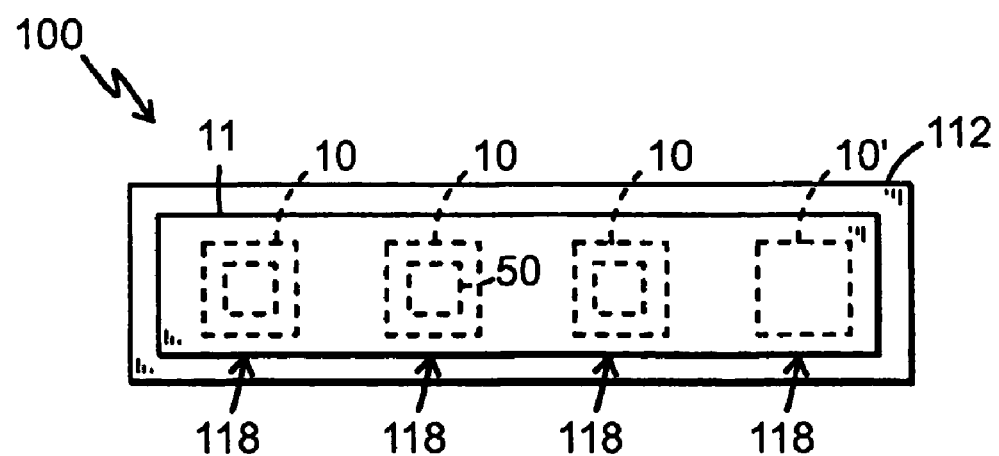
FIG. 9 is a plan view of a connecting station of FIG. 8 receiving a battery of cells.

In the embodiment of FIG. 9, there is shown a battery 11 of multiple cells 10 in a common housing adapted to occupy all sockets 118 and having mutually different coatings (not shown) on the electrodes 50 and/or compartment walls. Optionally, one or more cells 10 in the battery 11 may also be dummy cells 10', as desired.

Returning to FIG. 1a, the flowing unit 70 is composed of a fluid distributing system including fine caliber tubing and valves having small dead volumes to handle the usually small volumes of test solution 83 that are obtained, for example by condensation of an evaporated volume of air that may contain the analyte to be detected by the system of the invention. Example of tubing is standard HPLC PEEK (polyetheretherketone) or stainless steel tubing having an inner diameter of 0.25 mm to achieve acceptable sample dispersion and yet not too large pressure loss in the system.

The flowing unit 70 is designed and adapted to operate as follows: A valve arrangement comprising valves 86 for loading and introducing the plug of solution 83 between ends of the solution 75 is shown in two different positions in FIG. 1a and FIG. 1b. While other valve arrangements are conceivable to fulfill the desired functions, the valve 86 used in the preferred embodiment is a Cheminert® Model C6 Port Switching Valve marketed by Valco Instruments Co. Inc. The valve arrangement 86 operates as follows:

In the first position shown in FIG. 1a, valve 86 allows introducing the test solution 83 to a loop 90 of tubing from an injector 82 via a line 84 to form the plug of test solution. At this stage, valve 86 directs loop 90 to a waste line 96 until the injection of the plug of test solution 83 is completed so that a portion of the solution 75 in front of the plug in loop 90 is received by a waste reservoir 94.

In the second valve position shown in FIG. 1b, valve 86 connects the loop 90 through a line 78 to a solution feeding unit 72 comprising a reservoir 74 containing the solution 75 and a pump 76.

It is very important that the flow through the cell compartments 34 has a steady flow with little or no pulsations in order not to affect oscillating characteristics, such as resonant frequency, of the crystal(s) 50. The pump 76, for instance a peristaltic pump, should therefore have a minimum of pulsations. The pump is preferably a low flow rate (5-500 µl/min), low pressure pump delivering a stable flow pressure and flow rate. An important component of the feeding unit 72 is a pulse dampener 80, which stabilizes the flow and reduces pulses from the pump 76 as well as eliminates air bubbles in the flow. The pulse dampener 80 comprises a partially filled closed container (volume about 2 ml) for accumulating a volume of the flowing solution 75 together with a possibly pressurized compressible fluid.

In the second valve position, the plug of test solution 83 is now trapped between volumes of solution 75. Valve 86 connects loop 90 to line 98. By continuing action of pump 76 the plug of test solution in the loop 90 will now be introduced to the connecting station 100 and to the compartments 34 (FIG. 6) of the cells connected to the panel 112 such that the analyte(s) possibly present in the flow will interact with the coatings. At this moment, also the power and measurement electronics 130 starts the detection process as described.

The flow line 78, 90, 98 may further comprise a particle filter to ensure that no possibly disturbing particles in the solutions 75, 83 enter the cells (10).

EXAMPLES

An analysis system was prepared for displacement reaction by surface coating of metal surfaces on electrodes of piezoelectric crystals with their respective antigens that are derivatives of analyte antigens that are to be detected. Each coating antigen has a weaker affinity to an antibody than the analyte antigen in solution. The coated crystals were inserted into the cell housing and thereafter docked to the flowing system. The pump was turned on and the pulse dampener was filled with solution to half its volume. The system was allowed to stabilize during ten to 30 minutes, until the frequency baselines had a drift below 2 Hz/min and a noise level below 1 Hz.

Figure 10:
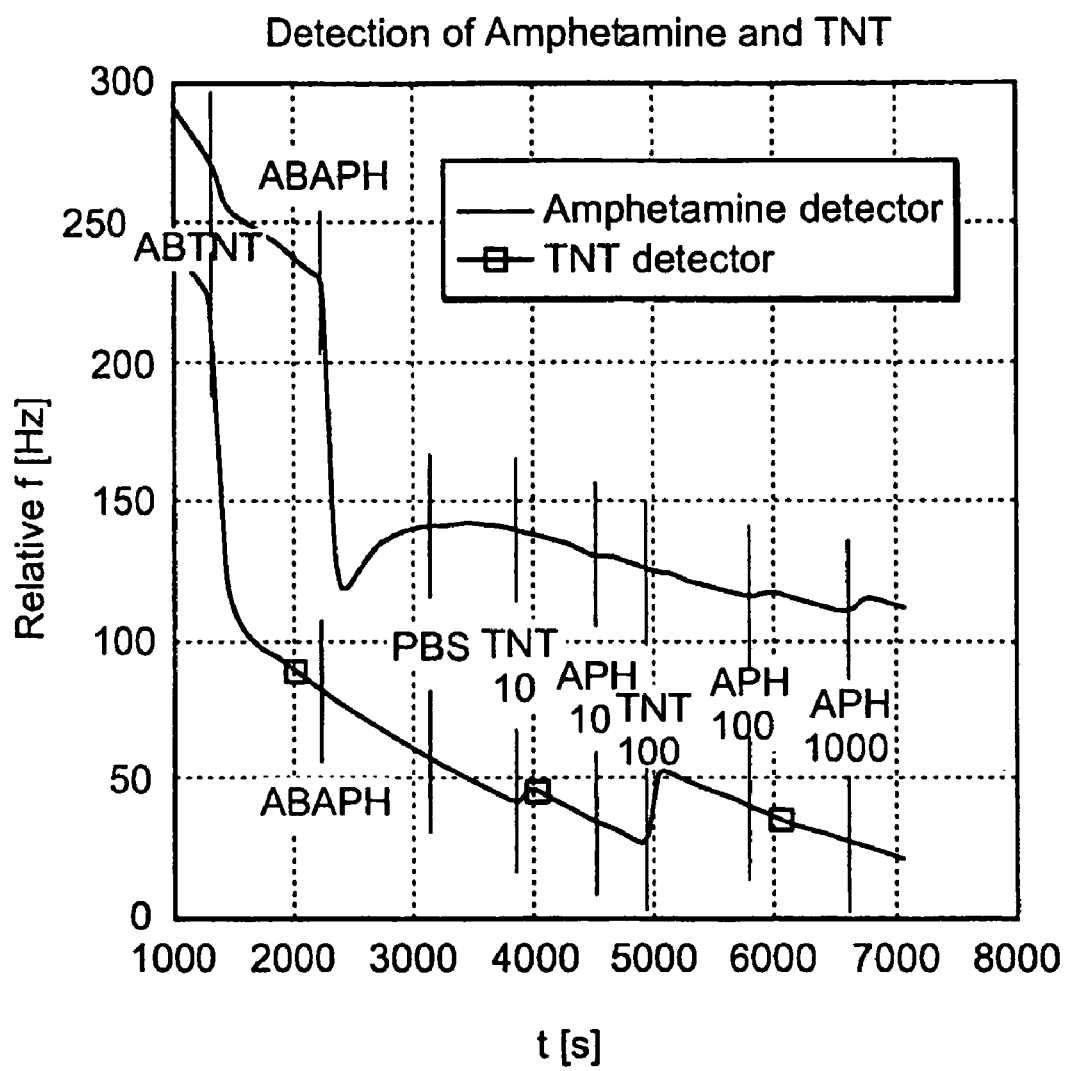
FIG. 10 is a diagram showing the individual response of two serially connected sensor cells.
Figure 11:
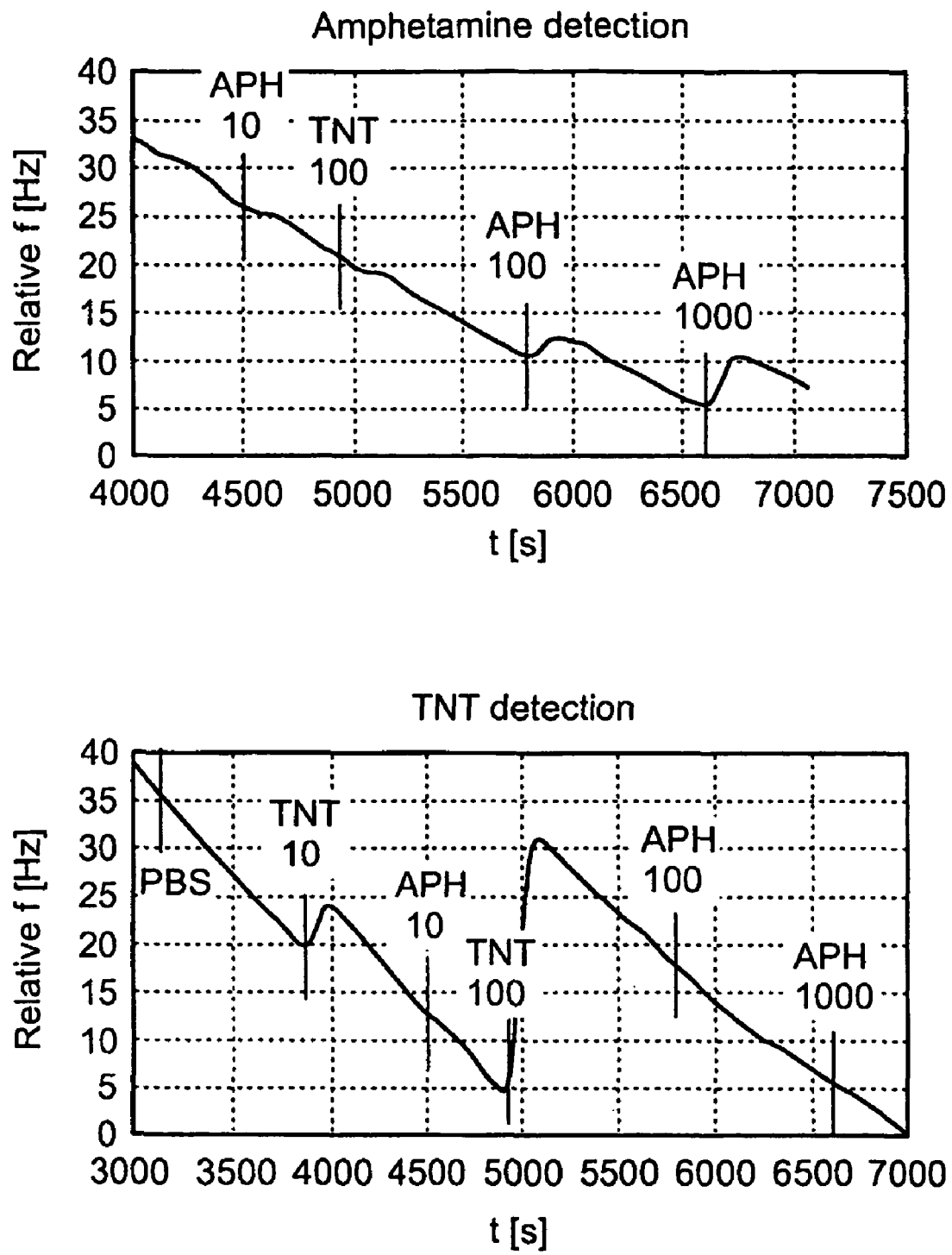
FIG. 11 is another diagram showing the individual response of two serially connected sensor cells.

Antibodies (AB) of 0.02 g/l against the substances to be detected (analytes) and the coating antigens were injected into the system with the 100 µl loop. Negative frequency shifts of 50 to 200 Hz of the crystals were observed at their respective AB-injection (see FIGS. 10 and 11). When the antibodies had been loaded onto the antigen-containing coating on the metal surfaces, the system was ready for detection. A sample, containing one of the two substances (concentrations 10-1000 pg/µl) were injected via the sample loop. As can be seen in FIGS. 10 and 11 the crystals with the corresponding antibodies received a positive frequency shift of 5-50 Hz depending on the injected concentration.

FIG. 10 shows the individual response of two serially connected sensor cells. Cell No. 1 is an amphetamine cell and reacts on samples containing amphetamine but not TNT. Cell No. 2 is a TNT cell and reacts only at the presence of TNT but not amphetamine.

FIG. 11 corresponds to FIG. 10 but is reversed. Cell No. 1 is a TNT cell and Cell No. 2 is an amphetamine cell.

The relevant data in the detection of amphetamine and TNT using a series flow cell system based on QCM (Quartz Crystal Microbalance) technology were as follows:

Flow rate: 100 µL/min
Injection volume: 100 µL
Rubber gasket (O-ring): Viton 5.8
Antigen fc1 (FIG. 11): TNT PAG25
Antigen fc2 (FIG. 11): Amphetamine B002
Abbreviations:
PBS Phosphate saline buffer pH 7.4
TNT Trinitrotoluene
APH Amphetamine
ABTNT Antibodies with specificity for TNT
ABAPH Antibodies with specificity for Amphetamine The concentrations of ABTNT and ABAPH were 0.02 g/L. The concentrations of TNT and amphetamine are given in pg/µL. The running buffer was PBS pH 7.4.

In a similar manner the possible presence of MDMA (Ecstasy), Heroin, Amphetamine, and cocaine, respectively, in test aliquots (injection volumes) were tested with a multiple piezoelectric crystal microbalance device of the invention with serially connected sensor cells.

Flow rate: 100 µL/min
Injection volume: 50 µL

The individual results of relative frequency change [Hz] plotted against time [s] are given in FIGS. 12, 13, 14 and 15.

Figure 12:
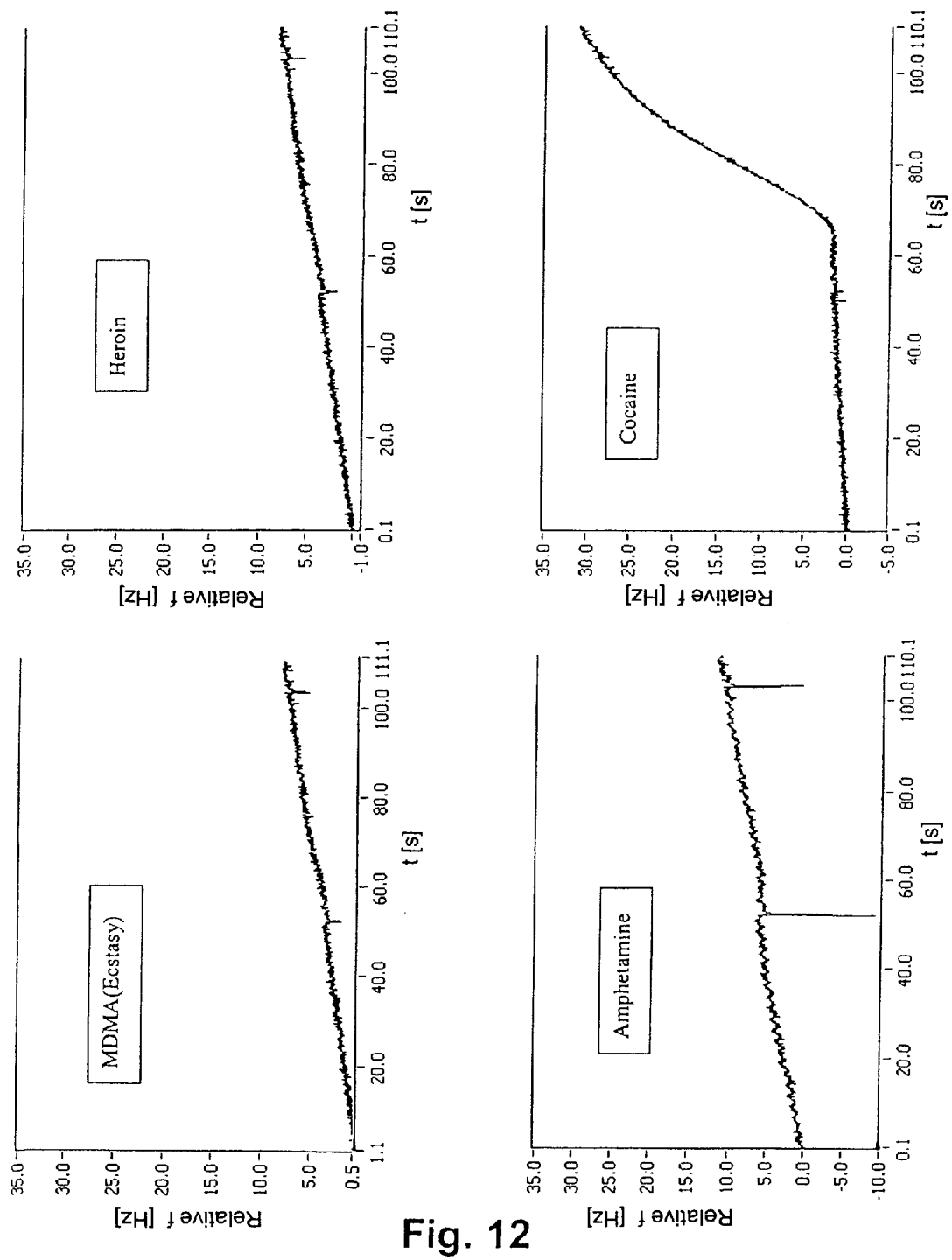
FIGS. 12, 13, 14 and 15 show each read-outs of the results from a multiple piezoelectric crystal microbalance device of the invention with serially connected sensor cells showing four individual diagrams of responses with regard to possible presence of MDMA (Ecstasy), heroin, amphetamine, and cocaine, respectively. The relative frequency change [Hz] is plotted against time [s].

FIG. 12. Injection of a cocaine (10 pg/mikroliter) in a multicell configuration that is sensitive against MDMA, amphetamine, heroin and cocaine.

Figure 13:
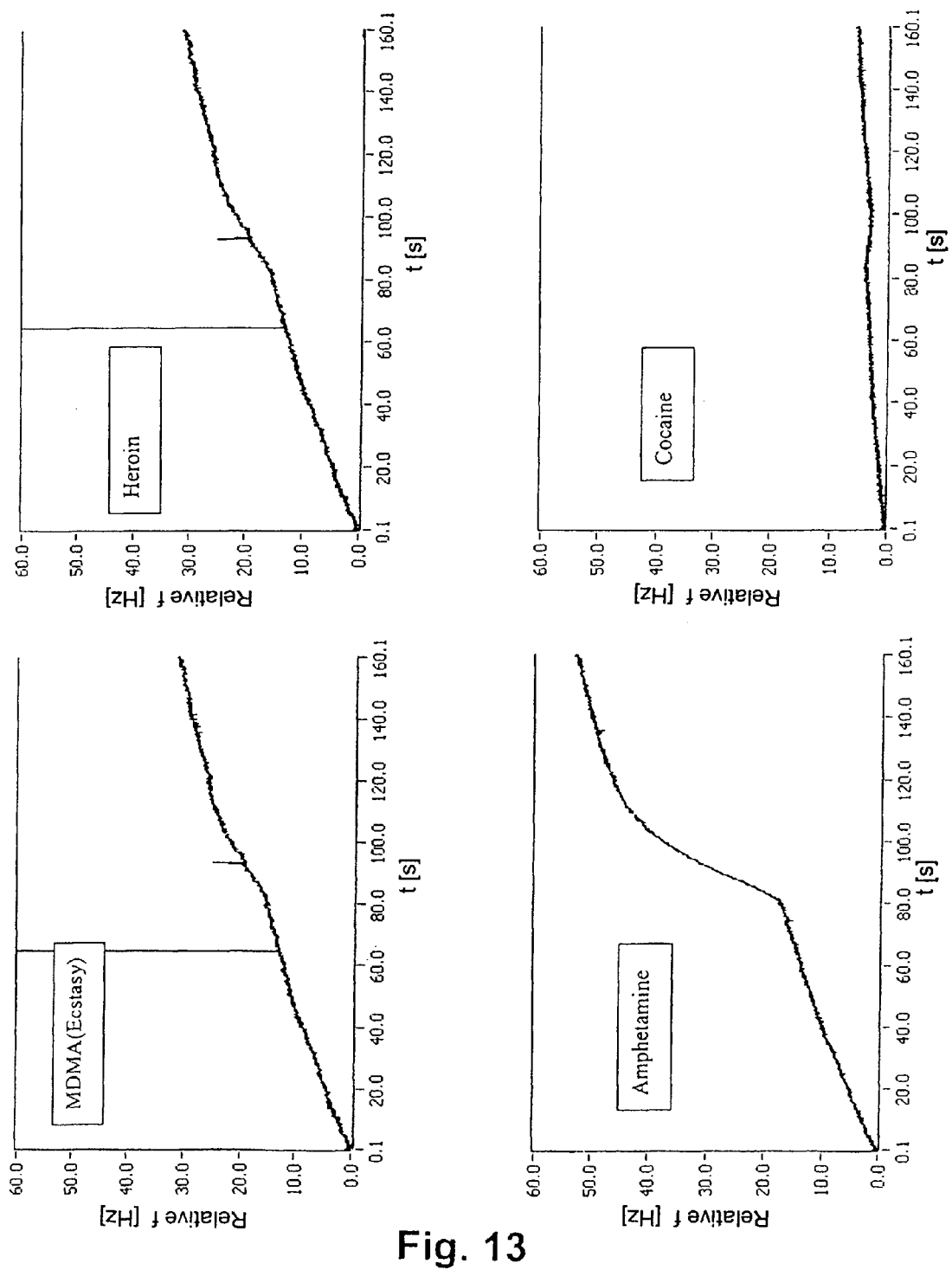
Figure 14:
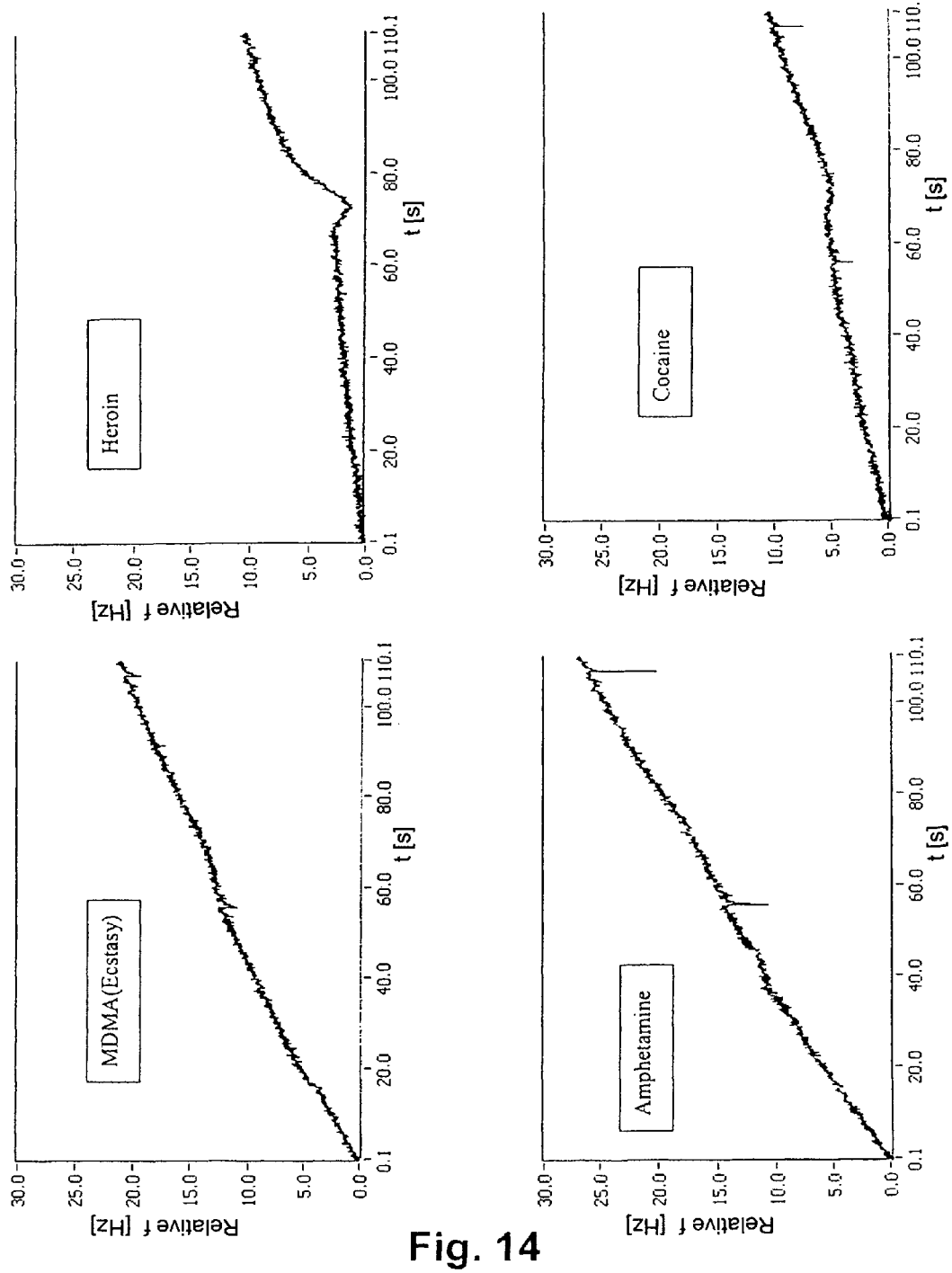
Figure 15:
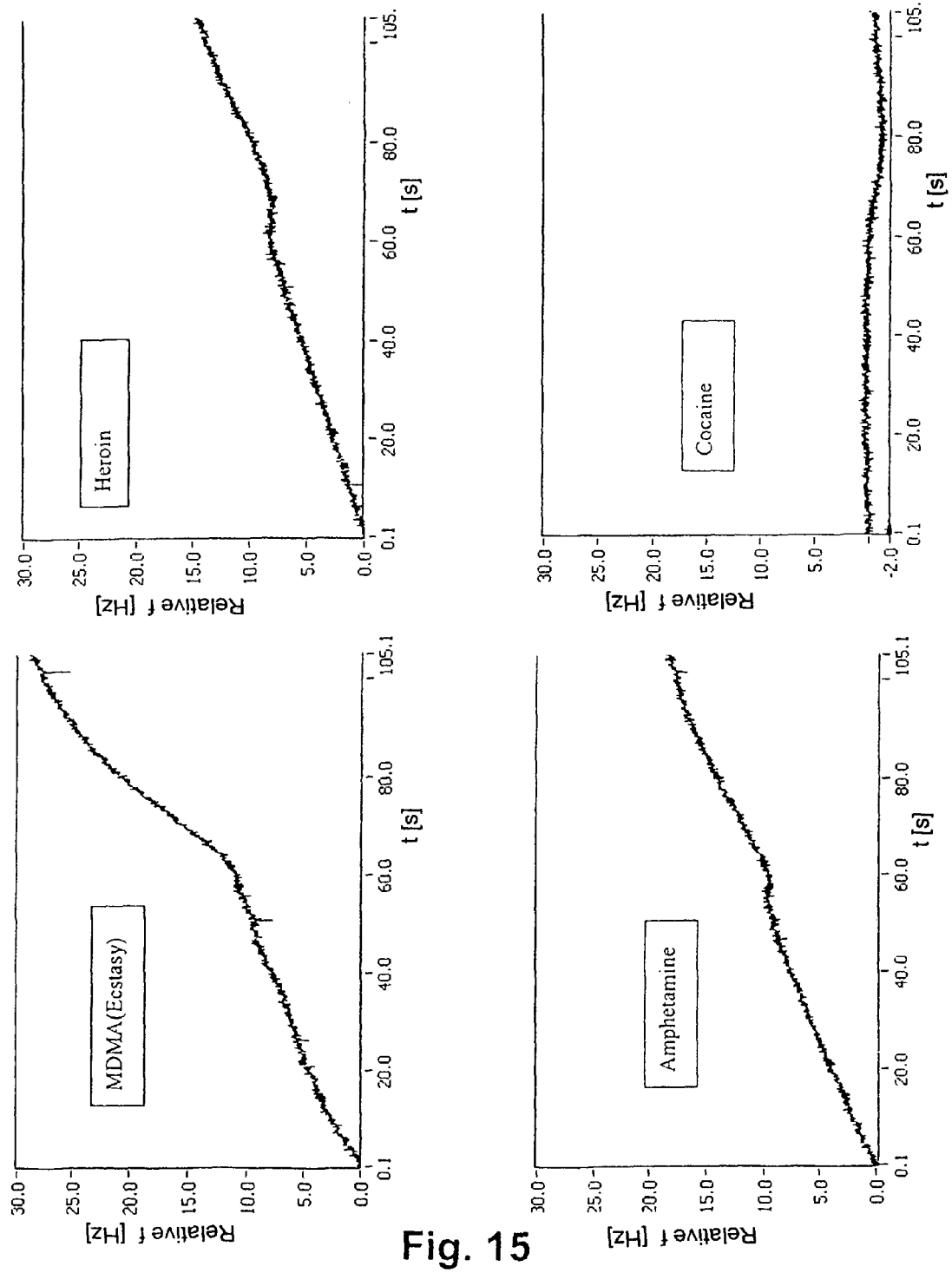

FIG. 13. Injection of amphetamine (10 pg/mikroliter) in a multicell configuration that is sensitive against MDMA, amphetamine, heroin and cocaine FIG. 14. Injection of heroin (10 pg/mikroliter) in a multicell configuration that is sensitive against MDMA, amphetamine, heroin and cocaine FIG. 15. Injection of ecstasy (10 pg/mikroliter) in a multicell configuration that is sensitive against MDMA (ecstasy), amphetamine, heroin and cocaine As can be seen from the FIGS. 12, 13, 14 and 15, each individual cell reacts only with the substance (antigen) that the cell is designed for.

The invention claimed is:

1. A multiple piezoelectric crystal microbalance device comprising a connecting station (100,101) for receiving and individually operating an array of piezoelectric crystal microbalances and a plurality of individually detachable piezoelectric crystal microbalance flow-through cells for engaging with the connecting station, wherein the connecting station comprises:
   a connecting panel (112; 113) having an array of cell connecting receptors (118), each cell connecting receptor comprising a receptor connector portion (120) for automatic mating operative engagement with a cell connector portion (24) of said piezoelectric crystal microbalance flow-through cell (10) upon plugging said flow-through cell (10) into the connecting station (100,101), and wherein the receptor connector portion (120) comprises:
   a pair of electric connecting ports (126, 128) for communication with a power and measurement means (130) for oscillating a piezoelectric crystal (50) carrying two electrodes (56,62) in a cell compartment (34) of one operatively engaged flow-through cell (10) and for measuring oscillating characteristics of the piezoelectric crystal (50); and
   a pair of fluid connecting ports (122, 124) for communication with flowing means (70) for uninterrupted flowing of a solution (75) and a test solution aliquot (83) to, and through, the cell compartment (34);
   wherein the individually operated piezoelectric crystal microbalances are electrostatically and electromagnetically shielded from each other; and
   further comprising grounding means (108) for electrical grounding of the flow solution (75) and the test solution aliquot (83) to the cell compartment (34) of each of the flow-through cells (10).

2. The multiple piezoelectric crystal microbalance device according to claim 1, wherein the connecting station (100) comprises connection means (112) for serial interconnection of the flowing of the solution (75) and test solution aliquot (83) to and through the cell compartment (34) of the individual flow-through cells (10).

3. The multiple piezoelectric crystal microbalance device according to claim 1, wherein the connecting station (101) comprises connection means (113) for parallel connection of the flowing of the solution (75) and test solution aliquot (83) to and through the cell compartment (34) of the individual flow-through cells (10).

* * * * *